(12) United States Patent
Rizik

(10) Patent No.: US 10,569,077 B2
(45) Date of Patent: *Feb. 25, 2020

(54) REDUCED LARSEN EFFECT ELECTRODE

(71) Applicant: Alpha Omega Neuro Technologies Ltd., Nazareth (IL)

(72) Inventor: John Rizik, Kfar-Reine (IL)

(73) Assignee: Alpha Omega Neuro Technologies Ltd., Nazareth (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/175,941

(22) Filed: Oct. 31, 2018

(65) Prior Publication Data

US 2019/0060635 A1    Feb. 28, 2019

Related U.S. Application Data

(63) Continuation of application No. 15/308,374, filed as application No. PCT/US2016/026536 on Apr. 7, 2016, now Pat. No. 10,143,836.

(60) Provisional application No. 62/144,042, filed on Apr. 7, 2015.

(51) Int. Cl.
    *A61B 5/04* (2006.01)
    *A61N 1/00* (2006.01)
    *A61N 1/05* (2006.01)

(52) U.S. Cl.
    CPC ............ *A61N 1/05* (2013.01); *A61B 5/04001* (2013.01); *A61N 1/0534* (2013.01)

(58) Field of Classification Search
    CPC ...... A61B 18/1492; A61B 2018/00577; A61B 5/14865; A61B 18/1477; A61B 2018/00267; A61B 5/0422; A61B 2018/00351; A61B 2018/1475; A61B 17/3421; A61B 5/0006; A61B 2017/3484
    USPC ........ 600/372–378, 381, 393, 481, 508–509; 606/20–42; 607/115–116, 119, 122–123
    See application file for complete search history.

(56) References Cited

U.S. PATENT DOCUMENTS

| | | |
|---|---|---|
| 5,741,225 A | 4/1998 | Lax et al. |
| 5,906,613 A | 5/1999 | Mulier et al. |
| 5,993,447 A | 11/1999 | Blewett et al. |
| 6,902,572 B2 | 6/2005 | Beulke et al. |
| 7,033,326 B1 | 4/2006 | Pianca et al. |
| 7,179,522 B2 | 2/2007 | Hiel et al. |
| 7,582,058 B1 | 9/2009 | Miles et al. |
| 8,340,783 B2 | 12/2012 | Sommer et al. |
| 8,361,013 B2 | 1/2013 | Wood, Jr. |

(Continued)

FOREIGN PATENT DOCUMENTS

| | | |
|---|---|---|
| EP | 1273922 | 1/2003 |
| EP | 2552536 | 2/2013 |

(Continued)

OTHER PUBLICATIONS

Applicant-Initiated Interview Summary dated Oct. 20, 2017 From the US Patent and Trademark Office Re. U.S. Appl. No. 15/308,374. (3 pages).

(Continued)

*Primary Examiner* — Joseph A Stoklosa
*Assistant Examiner* — Brian M Antiskay

(57) ABSTRACT

The disclosure relates to a reduced Larsen Effect electrode. Specifically, the disclosure relates to an electrode with an insulation-coated electrode wire coaxially surrounded over a substantial portion thereof, by predetermined assembly of alternating rigid and isolating layers.

20 Claims, 9 Drawing Sheets

(56) References Cited

U.S. PATENT DOCUMENTS

| | | |
|---|---|---|
| 8,755,906 B2 | 6/2014 | Moffitt et al. |
| 2003/0216771 A1 | 11/2003 | Osypka et al. |
| 2007/0106143 A1 | 5/2007 | Flaherty |
| 2017/0050014 A1 | 2/2017 | Rizik |

FOREIGN PATENT DOCUMENTS

| | | |
|---|---|---|
| WO | WO 2014/142741 | 9/2014 |
| WO | WO 2016/164650 | 10/2016 |

OTHER PUBLICATIONS

International Preliminary Report on Patentability dated Oct. 19, 2017 From the International Bureau of WIPO Re. Application No. PCT/US2016/026536. (7 Pages).
International Search Report and the Written Opinion dated Jul. 25, 2016 From the International Searching Authority Re. Application No. PCT/US2016/026536.
Notice of Allowance dated Aug. 9, 2018 From the US Patent and Trademark Office Re. U.S. Appl. No. 15/308,374. (7 pages).
Official Action dated Mar. 26, 2018 From the US Patent and Trademark Office Re. U.S. Appl. No. 15/308,374. (18 pages).
Official Action dated Jun. 30, 2017 From the US Patent and Trademark Office Re. U.S. Appl. No. 15/308,374. (16 pages).
Communication Pursuant to Article 94(3) EPC Dated Oct. 22, 2019 From the European Patent Office Re. Application No. 16721539.1. (5 Pages).

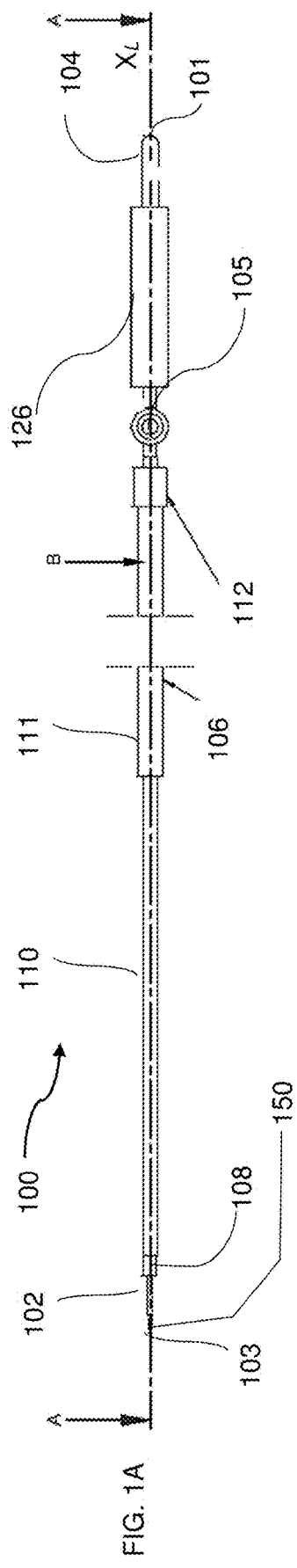
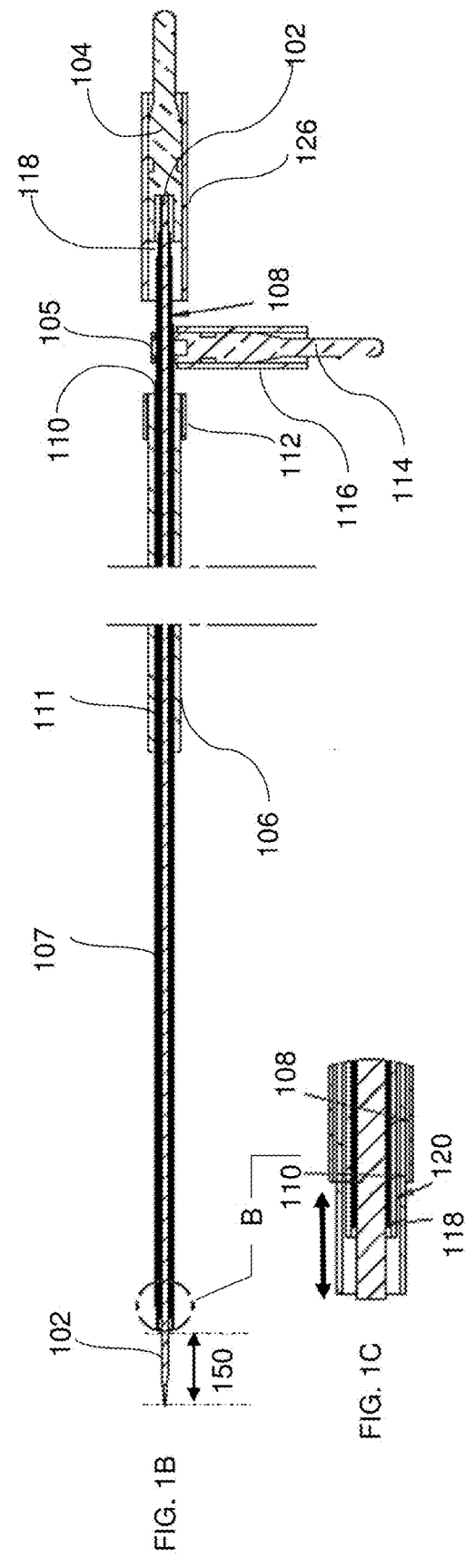
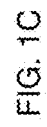
FIG. 1A
FIG. 1B
FIG. 1C

REDUCED LARSEN EFFECT ELECTRODE

RELATED APPLICATIONS

This application is a continuation of U.S. patent application Ser. No. 15/308,374, filed on Nov. 2, 2016, which is a National Phase of PCT Patent Application No. PCT/US2016/026536 having International filing date of Apr. 7, 2016, which claims the benefit of priority under 35 USC § 119(e) of U.S. Provisional Patent Application No. 62/144, 042, filed on Apr. 7, 2015. The contents of the above applications which are all is incorporated herein by reference as if fully set forth herein in their its entirety.

BACKGROUND

The disclosure is directed to a reduced Larsen Effect electrode. Specifically, the disclosure is directed to an electrode with an insulation-coated electrode wire coaxially surrounded over a substantial portion thereof, by predetermined configuration of alternating rigid and isolating (or vibration dampening) layers.

Depth electrode recording systems are typically used in localizing surgical targets for implantation of depth electrodes or for stimulating and recording electrical signals from target regions in a tissue or organ. Typically, these systems are in communication with depth electrodes which are used for temporary stimulation and/or recording of electrical signals within a localized surgical site of a subject.

Commercially available depth electrodes are typically characterized by a high sensitivity for external noises with substantial microphonic feedback effect between the system speakers and the depth electrode, which impedes signal integrity received from the depth electrode.

The microphonic feedback effect can be caused by at least one of the following: positive feedback is generated once the speakers feedback to the electrode and as a result saturates the amplifiers. Various mechanical noise and vibration, such as motor vibration, motion of the electrode within the tissue or voice of the subject, are detected by the electrode that acts essentially as a microphone and is erroneously combined with the neural signal that is being recorded. It refers to the repercussion of the reception on the transmission, or of the output on the input, phenomenon which is self-maintained in a closed loop (hereinafter, "Larsen Effect"), sometime to saturation.

Accordingly, accurate and high signal integrity (signal to noise ratio) of the electrode, is important in order to improve the effectiveness and efficiency of the electrode. Thus, there is a need in the field to provide an electrode with reduced sensitivity to acoustic feedback.

SUMMARY

Provided herein are embodiments of reduced Larsen Effect electrodes.

In an embodiment, provided herein is a reduced Larsen Effect electrode assembly for stimulation and/or recording of electrical signals in a tissue or organ of a subject, the reduced Larsen effect Electrode having a longitudinal axis, a distal end and a proximal end comprising: a shielding tube having an open proximal end and an open distal end, with an open stopper operably coupled to the distal end of the shielding tube; a macro electrode sub-assembly coaxially coupled within the shielding tube, comprising: a rigidity-imparting macro cannula; and an isolating macro sleeve coaxially coupled thereon; and a micro electrode sub-assembly coaxially, slidably coupled within the macro electrode assembly, comprising an insulation-coated electrode wire coaxially coupled along a portion thereof; to an isolating micro sleeve, coaxially coupled within a rigidity-imparting micro cannula In yet another embodiment, the reduced Larsen Effect electrodes provided, are configured such that at a fixed amplitude, the reduced Larsen Effect electrode produces noise level of no more than ±25 µV over frequency range between 0.1 Hz and 7.0 kHz.

BRIEF DESCRIPTION OF THE DRAWINGS

The features of the reduced Larsen Effect electrode assembly relating thereto described herein, will become apparent from the following detailed description when read in conjunction with the drawings, which are exemplary, not limiting, and wherein like elements are numbered alike in several figures and in which.

Figure 1D:
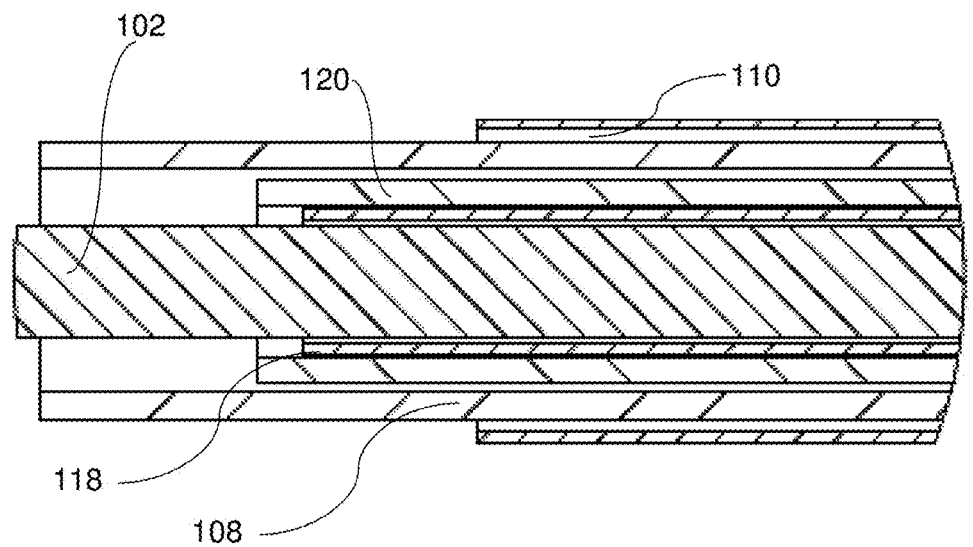
FIG. 1A is a side view illustration of an embodiment of the reduced Larsen Effect electrode, with X-Z cross section taken along A-A in FIG. 1A illustrated in FIG. 1B and enlarged portion B illustrated in FIG. 1C, with Z-Y cross section c in FIG. 1A, illustrated in FIG. 1D.

While the disclosure is amenable to various modifications and alternative forms, specifics thereof have been shown by way of example in the drawings and will be further described in detail hereinbelow. It should be understood, however, that the intention is not to limit the disclosure to the particular embodiments described. On the contrary, the intention is to cover all modifications, equivalents, and alternatives.

DETAILED DESCRIPTION

The disclosure relates in one embodiment to reduced Larsen effect electrodes.

The disclosure provides for an electrode with an insulation-coated electrode wire coaxially surrounded over a substantial portion thereof, by predetermined assembly of alternating rigid and isolating (or vibration dampening) layers. In other words, a depth electrode or multi electrode array, which is resistant to microphonic feedback effect caused by one or more of the following and their combination; a positive feedback is generated once the speakers feedback to the electrode and as a result saturates the amplifiers. Various mechanical noise and vibration, such as motor vibration, motion of the electrode within the tissue or voice of the subject, are detected by the electrode that acts as a microphone and is erroneously combined with the neural signal that is being recorded.

Accordingly, provided herein is an electrode for stimulating or recording of electrical signals while reducing Larsen effect, which can have a micro electrode sub-assembly comprising in an embodiment, an insulation-coated electrode wire with an isolating (and/or vibration dampening) sleeve thereon, inserted in a rigidity-imparting micro cannula. The rigidity-imparting can also be configured to provide protection against electromagnetic interference (EMI), electrostatic discharge (ESD), and radiofrequency interference (RFI). (As subsequently used herein "EMI" shall include ESD, RFI, and any other type of electromagnetic emission or effect). In addition, the rigidity-imparting micro cannula decreases the flexibility of the wire, preventing the building of a resonant wave in response to exposure to vibration resulting from acoustic pressure on the electrode wire. The term "rigidity-imparting" represents the ability of the cannula to provide a degree of strength against bending or in other words, flexure rigidity.

The micro electrode sub-assembly is coaxially inserted into a macro electrode assembly such that the micro electrode sub assembly is selectably slidably (in other words, telescopic sliding of the micro electrode sub-assembly within the macro electrode sub-assembly does not affect the ability of the reduced Larsen effect electrode assembly) coupled and can be telescopically extended and retracted to provide variable sensing zone, or tip. The macro electrode sub-assembly is compiled in the reverse order of the micro electrode assembly. In other words, a rigidity-imparting macro cannula has a sleeve of an isolating macro tube. The outer diameter of the rigidity-imparting micro cannula can be configured to be between about 0.005 mm and 0.2 mm smaller than the inner diameter of the rigidity-imparting macro tube, thereby, leaving annular space between the rigidity-imparting tubes. Accordingly and in an embodiment, the rigidity-imparting micro tube and the rigidity-imparting macro cannula are separated by an annular space over a substantial portion of the longitudinal axis of the macro electrode sub-assembly (which is shorter than the micro electrode assembly)

Accordingly and in an embodiment, provided herein is a reduced Larsen Effect electrode assembly for stimulation and/or recording of electrical signals in a tissue or organ of a subject, the reduced Larsen effect Electrode having a longitudinal axis, a distal end and a proximal end comprising: a shielding tube having an open proximal end and an open distal end, with an open stopper operably coupled to the distal end of the shielding tube; a macro electrode sub-assembly coaxially coupled within the shielding tube, comprising: a rigidity-imparting macro cannula; and an isolating (and/or vibration dampening) sleeve coaxially coupled thereon; and a micro electrode sub-assembly coaxially, slidably coupled within the macro electrode assembly, comprising an insulation-coated electrode wire coaxially coupled along a portion thereof; to an isolating micro sleeve, coaxially coupled within a rigidity-imparting micro cannula.

In another embodiment, at least a portion of the macro electrode sub-assembly forming the reduced Larsen Effect electrode assemblies described herein, can extend distally beyond the stopper of the shielding tube. In other words, and as described, the stopper coupled to the shielding tube at the distal end can be open and the distal portion of the macro electrode sub-assembly can extend beyond (backwards or distally, away from the tip) the stopper, creating a distal extension. Moreover, the portion of the macro electrode sub-assembly extending distally beyond the stopper of the shielding tube can be rotatably coupled to a first elongated coupling member. In other words, the portion of the macro electrode sub-assembly extending distally beyond the stopper of the shielding tube can form a hinge upon which the elongated coupling member can be coupled, allowing for rotation of the elongated coupling member (coupling to a power source e.g., or a processing module) around the portion of the macro electrode sub-assembly extending distally beyond the stopper of the shielding tube. The first elongated coupling member extending therefore transverse (or, perpendicular) to the longitudinal axis of the reduced Larsen Effect electrode. As indicated, the first coupling member can be configured to communicate (or be in communication) with a first power source, a first transceiver or a first device comprising one or more of the foregoing. The device can be, for example a signal processor for receiving and analyzing the data recorded by the electrode, or provide the stimulation regimen required.

The term "signal processor" as used herein refers in an embodiment, to a power source, a pre-amplifier, an amplifier, an A/D and/or D/A converter, or a module or system comprising one or more of the foregoing. Likewise, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Further, term "communicate" (and its derivatives e.g., a first component "communicates with" or "is in communication with" a second component) and grammatical variations thereof are used to indicate a structural, functional, mechanical, electrical, or optical relationship, or any combination thereof, between two or more components or elements. As such, the fact that one component is said to communicate with a second component is not intended to exclude the possibility that additional components can be present between, and/or operatively associated or engaged with, the first and second components. Furthermore, the term "electronic communication" means that one or more components of the reduced Larsen Effect electrode assemblies described herein, are in wired or wireless communication or internet communication so that electronic signals and information can be exchanged between the components.

In addition, the first elongated coupling member used in the reduced Larsen Effect electrode assemblies described herein, can be further coupled to a first insulating band configured to cover a portion of the first elongated coupling member.

In an embodiment, at least a portion of the micro electrode sub-assembly used in the reduced Larsen Effect electrode assemblies described herein, can be configured to extend distally beyond the distal end of the macro electrode assembly. The portion of the micro electrode sub-assembly extending distally beyond the distal end of the macro electrode sub-assembly can be operably coupled to and be in communication with a second elongated coupling member, the second elongated coupling member extending coaxially with the longitudinal axis of the reduced Larsen Effect electrode wherein the second coupling member is configured to be in communication with a second power source, a second transceiver or a second device comprising one or more of the foregoing. For example, the first elongated coupling member can serve as a reference electrode and the second elongated coupling member can serve as the stimulating electrode. In an embodiment, both elongated coupling members (first and second), can be coupled to the same signal processor. Likewise, the first coupling member can be operably coupled and be in communication with the second power source, second transceiver or second device comprising one or more of the foregoing and vice-a-versa.

Further, the distal end of the portion of the micro electrode sub-assembly extending distally beyond the distal end of the macro electrode sub-assembly can be coupled to a micro collar.

In an embodiment, the insulation-coated electrode wire used in the reduced Larsen Effect electrode assemblies described herein, can be made of tungsten. Alternatively, the insulation-coated electrode wire used in the reduced Larsen Effect electrode assemblies described herein, can be made of platinum iridium, pure iridium, stainless steel or the like. Likewise, the shielding tube and/or the rigidity-imparting macro tube, and/or the rigidity-imparting micro tube used in the reduced Larsen Effect electrode assemblies described herein, can be made of stainless steel or the like. Furthermore, the isolating (and/or vibration dampening) macro sleeve and/or isolating (and/or vibration dampening) micro sleeve used in the reduced Larsen Effect electrode assemblies described herein, can be made of a biocompatible thermoplastic polymer. The biocompatible, thermoplastic polymer can be, for example; polyimide, polyurethane, poly(divinylfluroride), a polycarbonate, an acrylonitrile/butadiene/styrene copolymer, a poly ether-ether ketone (PEEK), an epoxy, a nylon, or a copolymer and/or derivative thereof comprising one or more of the foregoing.

Additionally, the rigidity-imparting macro cannula and/or isolating macro sleeve, used in the reduced Larsen Effect electrode assemblies described herein, can each have a wall thickness between about 0.01 mm and about 1 mm such that the rigidity-imparting macro cannula abuts the isolating macro sleeve along the entire length of the isolating macro sleeve. Similarly, the rigidity-imparting micro cannula and/or isolating micro sleeve used in the reduced Larsen Effect electrode assemblies described herein, can each have a wall thickness between about 0.01 mm and about 1 mm, such that the rigidity-imparting micro cannula abuts the isolating micro sleeve along the entire length of the rigidity-imparting micro cannula.

The reduced Larsen Effect electrode assemblies described herein, are configured to produces noise level of no more than ±25 µV over frequency range between 0.1 Hz and 7.0 kHz, more specifically, noise level of no more than ±10 µV over frequency range between 1.0 kHz and 4.0 kHz.

The depth probe described herein can be, for example, a stimulating and or recording electrode. Moreover, the reduced Larsen effect electrode, or electrode assemblies described herein can be configured to provide deep brain stimulation. Stimulating electrophysiological response and/or recording electrophysiological evoked response using the electrodes described herein can comprise stimulating, recording or both stimulating and recording signals differentially, single ended or both differentially and single ended. For example, a differential sensing configuration can include micro electrode sub-assembly as the sensing electrode and the macro electrode sub-assembly used as a reference electrode. Typical tip-to-ring (exposed sensing portion of the macro electrode assembly) spacing can be approximately 10 mm but may be greater or less than 10 mm. In an embodiment, the micro electrode sub-assembly of the reduced Larsen effect electrode assemblies provided herein, are configured to be slidably coupled to the macro electrode sub-assemblies, thus present variable measuring field length or, in other words, variable sensing portion (see e.g., element 150, FIGS. 1A, 1B, 7C, 8B).

Other differential sensing configurations using any type of available electrodes can be used. During differential sensing, both the sensing electrode and the reference electrode can be positioned along a mapped site, such as within a brain region or along a nerve branch, such that both electrodes are subjected to change in electrical potential caused by an electrophysiological event in the brain.

Likewise, single ended sensing electrode configurations can comprise a sensing electrode in contact with a region of interest, paired with a reference electrode placed away from the region of interest, such that the reference electrode is not initially subjected to changes in electrical potential caused by electrophysiological events occurring at the site. In these circumstances, the macro isolating sleeve and rigidity-imparting macro cannula forming the macro electrode sub-assembly of the reduced Larsen Effect electrode assemblies described herein can be configured to operate as a guide wire for the sensing, micro electrode sub-assembly (see e.g., element 107, FIG. 1B).

Recording the observation elements described herein can be configured to be performed between two adjacent macro-contacts, for example a tip contact and a ring macro contact spaced between about 20 µm and about 500 µm from the tip contact (or electrode) by, for example, recording differential local field potential (LFP) between the two contacts, wherein one contact is a reference to the other.

A more complete understanding of the components, processes, assemblies, and devices disclosed herein can be obtained by reference to the accompanying drawings. These figures (also referred to herein as "FIG.") are merely schematic representations (e.g., illustrations) based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Turning now to FIGS. 1A to 8B, illustrating reduced Larsen Effect electrode assembly 100 for stimulation or recording of electrical signals in a tissue or organ of a subject, reduced Larsen Effect electrode assembly 100 having longitudinal axis $X_L$, distal end 101 and proximal end 103 (see e.g., FIG. 1A). Reduced Larsen Effect electrode assembly 100 comprising: shielding tube 111 having open proximal end 131 and open distal end 133, with open stopper 112 (acting as a distal limit on the proximal movement of reduced Larsen Effect electrode assembly 100 in a holder—not shown), operably coupled to distal end 133 of shielding tube 111 forming stoppered shielding tube sub-assembly 106 (see e.g., FIG. 3B). Reduced Larsen Effect electrode assembly 100 further comprising macro electrode sub-assembly 130 having proximal end 127 and distal end 129 (see e.g., FIG. 2B) coaxially coupled within stoppered shielding tube sub-assembly 106, comprising rigidity imparting macro cannula 108 having isolating macro sleeve 110 coaxially coupled thereon (see e.g., FIGS. 1C, 2A). In an embodiment, isolating macro sleeve 108 can be a vibration dampening sleeve formed of a biocompatible thermoplastic polymer, or co-polymer. The term "vibration dampening" is intended to be representative of a sleeve which is capable of reducing vibrations in a sub-system. In another embodiment, stoppered shielding tube sub-assembly 106 is entirely missing and macro electrode sub assembly 130 may be configured not to operate as an electrode, but will rather operate as the shielding tube 107 (see e.g., FIG. 1B) whereby shielding tube 107 will be a guide and protect micro-electrode sub assembly 142 sensing zone 150 in proximal end 103. Under these circumstances and in another embodiment, reduced Larsen effect electrode assembly does NOT comprise first (or macro) elongated coupling member 114, first (or macro) elongated coupling member 114 extending transverse to longitudinal axis ($X_L$) of reduced Larsen Effect electrode assembly 100, and will only comprise elongated coupling member 104, second (micro) elongated coupling member 104 extending coaxially with longitudinal axis ($X_L$) of reduced Larsen Effect electrode assembly 100, operably coupled to the coated electrode wire 102 portion of micro electrode sub-assembly 142 extending distally beyond distal end 129 of macro electrode sub-assembly 130, through exposed isolating macro sleeve 118 at distal end 143 having rigidity-imparting cannula 120 extending beyond isolating macro sleeve 118, stoppered with micro collar 122, operating as a distal limit on the selectably slidable coupling of micro electrode sub assembly 142 within macro electrode sub-assembly 130. Accordingly and in an embodiment, micro collar 122 will abut distal end 129 on rigidity-imparting macro cannula 108 of macro electrode sub-assembly 130, thereby limiting the proximal movement of micro electrode sub assembly 142. The terms "selectably" or "selectably slidable" and similar grammatical configurations, refer in an embodiment to the user choice in altering sensing zone not affecting the operation of reduced Larsen Effect electrode assembly 100.

Figure 2A:
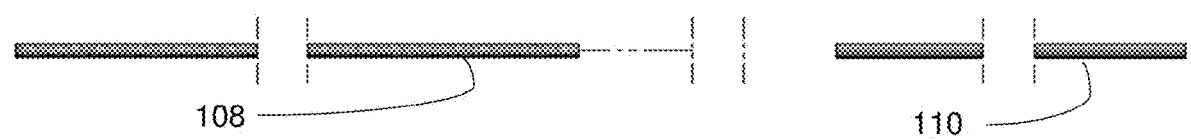
FIGS. 2A & 2B are respective simplified exploded view of a first assembly stage (FIG. 2A) of a first part of a macro electrode sub-assembly (FIG. 2B) of the reduced Larsen Effect electrode assembly shown in FIG. 1A.
Figure 2B:
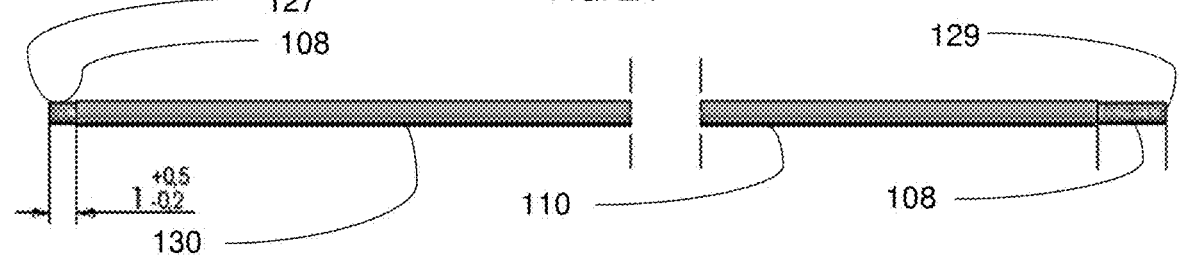
Figure 3A:
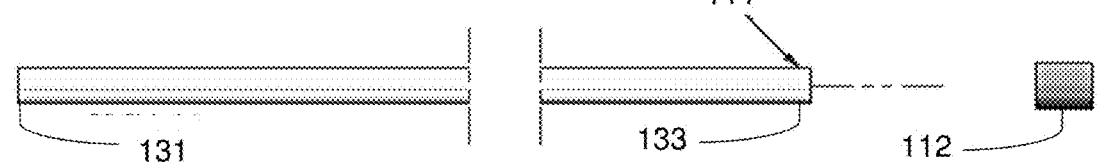
FIGS. 3A & 3B are respective simplified exploded view of the assembly stage of the shielding tube of the reduced Larsen Effect electrode assembly shown in FIG. 1A.
Figure 3B:
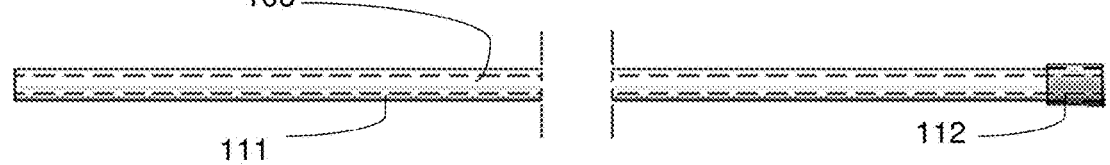
Figure 4A:
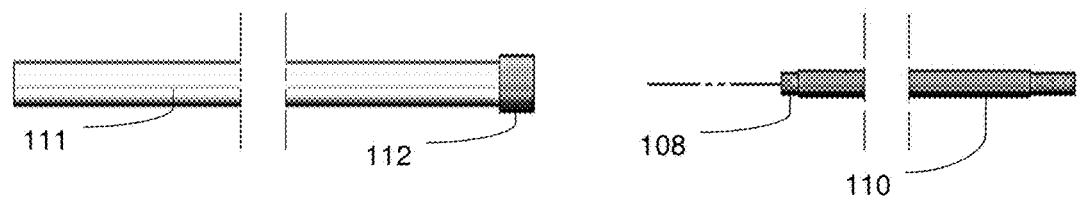
FIGS. 4A and 4B, illustrates the assembly of the macro electrode sub-assembly shown in FIG. 2B and the shielding tube illustrated in FIG. 3B.
Figure 4B:
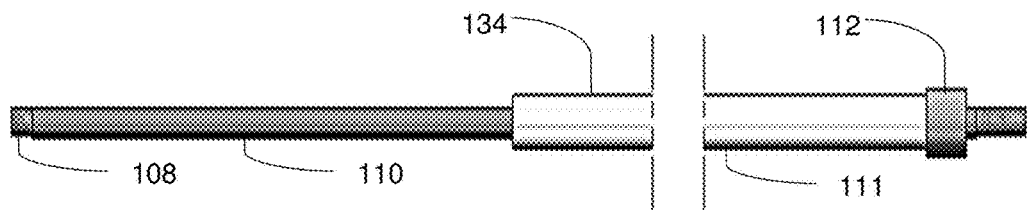
Figure 5:
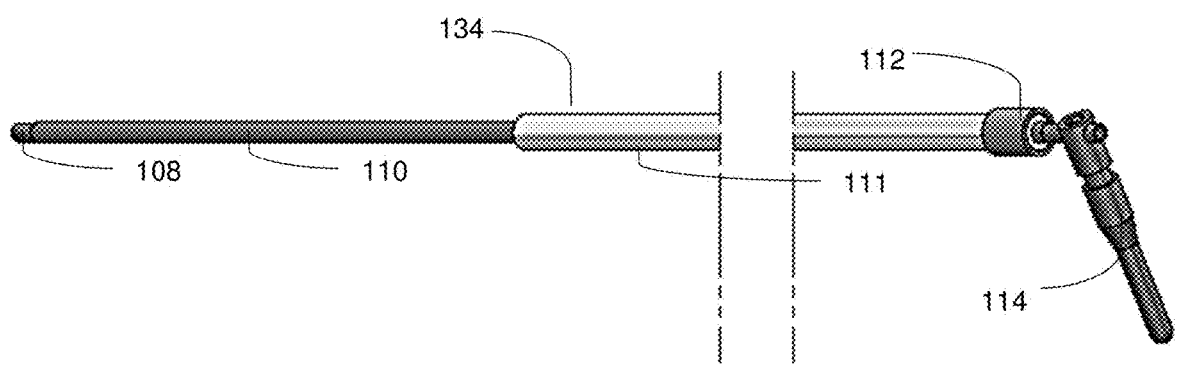
FIG. 5, illustrates the assembly of the elongated coupling member to the assembled shielding tube of FIG. 4B.
Figure 7A:
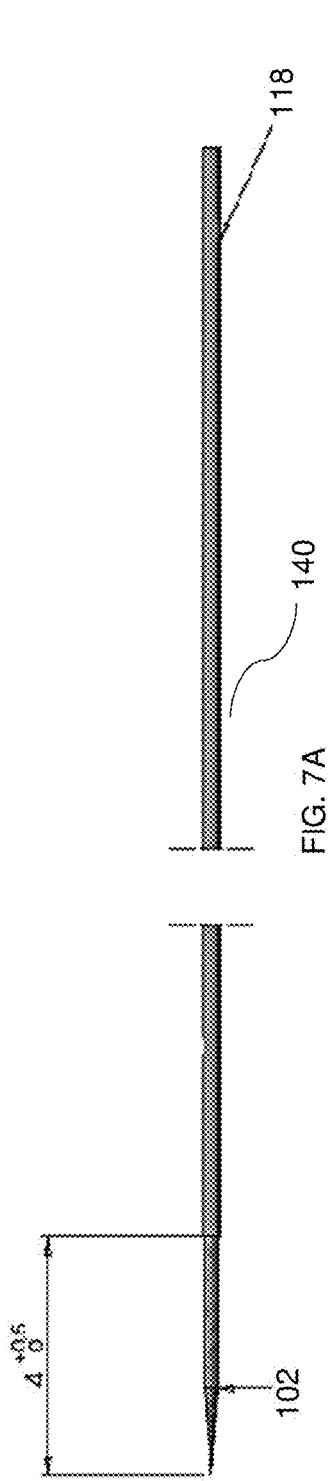
FIGS. 7A, 7B, and 7C illustrate the micro shielding assembly, of the depth electrode shown in FIG. 1A.
Figure 7B:
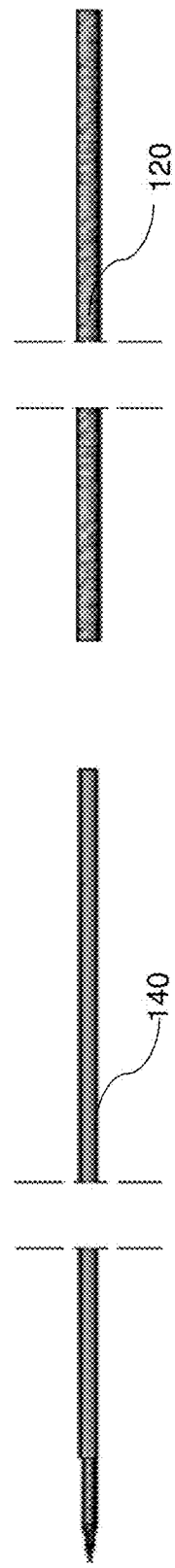
Figure 7C:
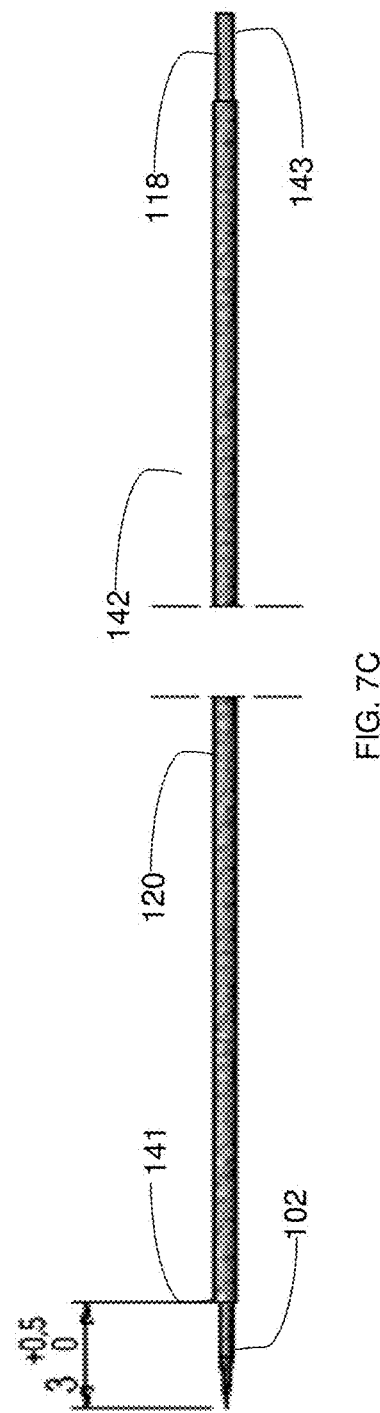
Figure 8A:
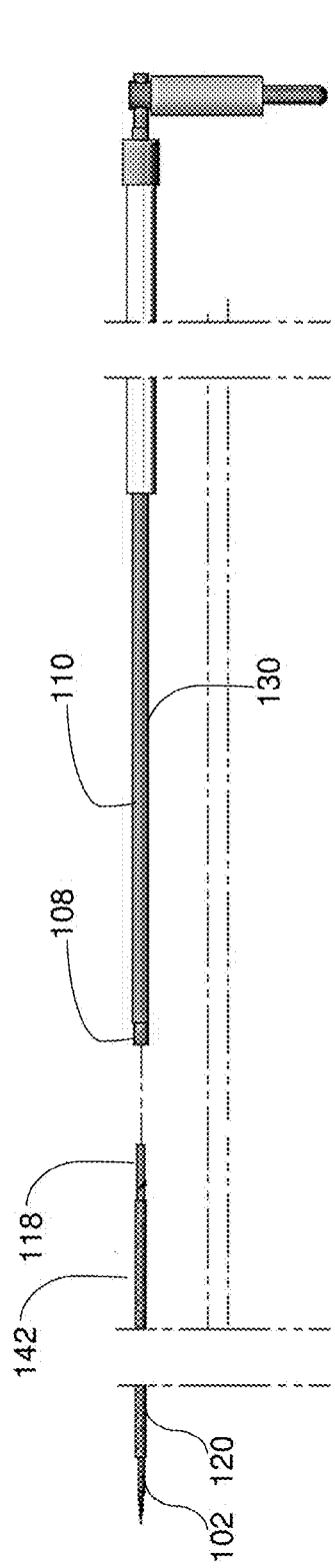
FIGS. 8A and 8B, illustrate the assembly of the micro electrode assembly into the macro electrode sub-assembly disposed within the shielding tube, attached to the banded elongated coupling member.
Figure 8B:
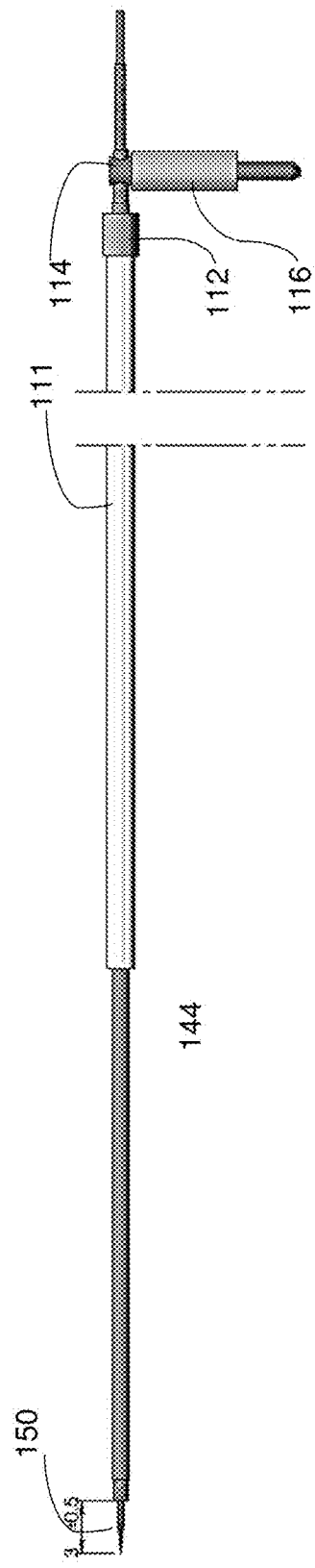

Alternatively, stoppered shielding tube sub-assembly 106 is entirely missing and macro electrode sub assembly 130 may be configured to operate as an additional electrode. Under these circumstances and in another embodiment, reduced Larsen effect electrode assembly does comprise first (or macro) elongated coupling member 114, first (or macro) elongated coupling member 114 extending transverse to longitudinal axis ($X_L$) of reduced Larsen Effect electrode assembly 100, as well as comprise elongated coupling member 104, second (micro) elongated coupling member 104 extending coaxially with longitudinal axis ($X_L$) of reduced Larsen Effect electrode assembly 100, operably coupled to the coated wire electrode 102 portion of micro electrode sub-assembly 142 extending distally beyond distal end 129 of macro electrode sub-assembly 130, through exposed isolating macro sleeve 118 at distal end 143 stoppered with micro collar 122 as described hereinabove As illustrated in FIG. 2B, as assembled, in macro electrode sub-assembly 130, rigidity imparting macro cannula 108 extend both proximally (for example, between about 0.1 mm and about 3.0 mm) and distally (for example, about 1.0 mm and about 10.0 mm) beyond isolating macro sleeve 110. Reduced Larsen Effect electrode assembly 100 further comprising micro electrode sub-assembly 142 (see e.g., FIG. 7C), coaxially, slidably coupled within macro electrode sub-assembly 130, micro electrode sub-assembly 142 having insulation-coated electrode wire 102 coaxially coupled along a portion thereof to isolating micro sleeve 118 (see e.g., FIG. 7A), which is coaxially coupled in rigidity-imparting micro cannula 120 (see e.g., FIG. 7B). In an embodiment, isolating micro sleeve 118 can be a vibration dampening sleeve formed of a biocompatible thermoplastic polymer, or co-polymer. As illustrated in FIGS. 7C (and 8B), proximal end 103 of micro electrode sub assembly 142 can be slidably coupled to macro electrode sub assembly 130, thus providing variable sensing zone 150.

Figure 6A:
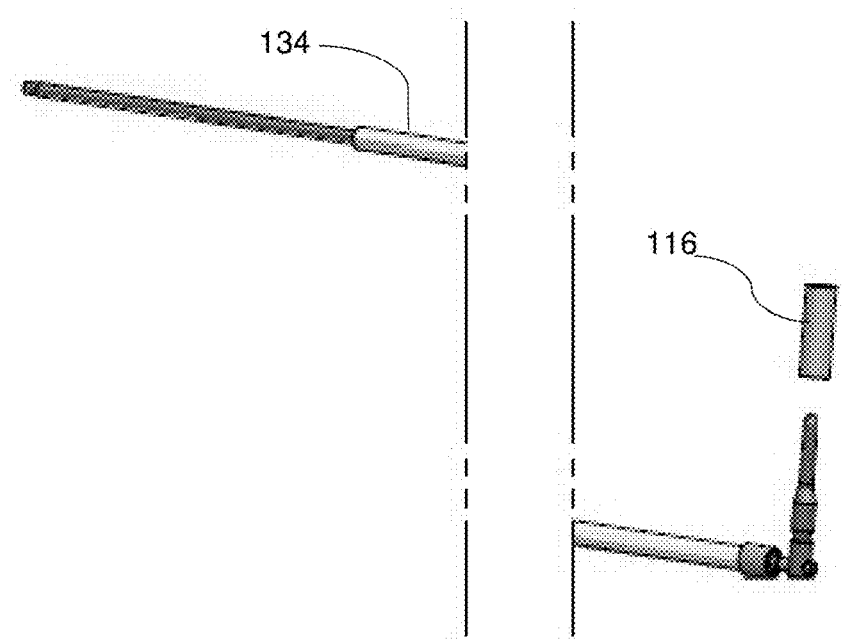
FIGS. 6A, 6B, illustrate the assembly of the insulating band onto the elongated coupling member illustrated in FIG. 5.
Figure 6B:
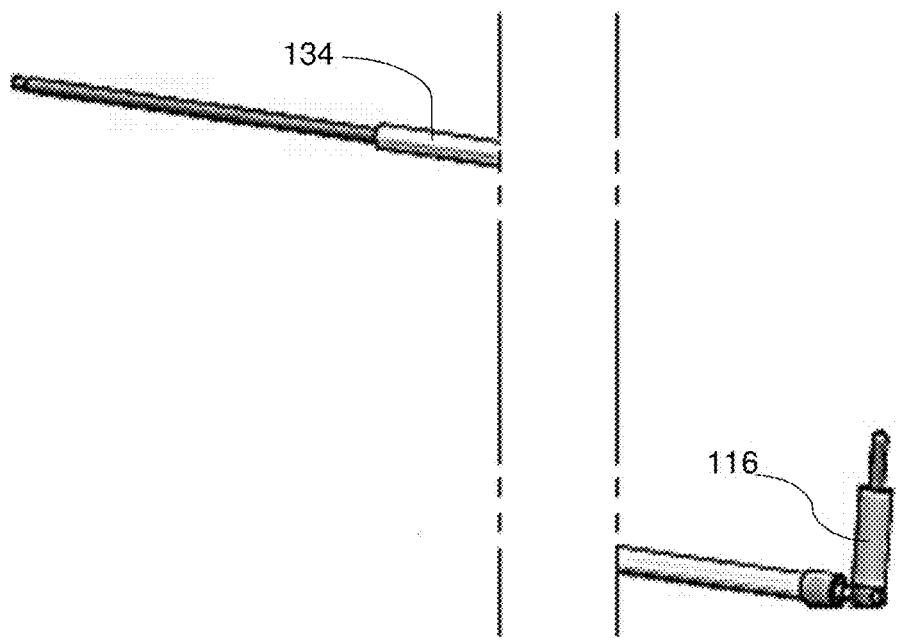
Figure 9A:
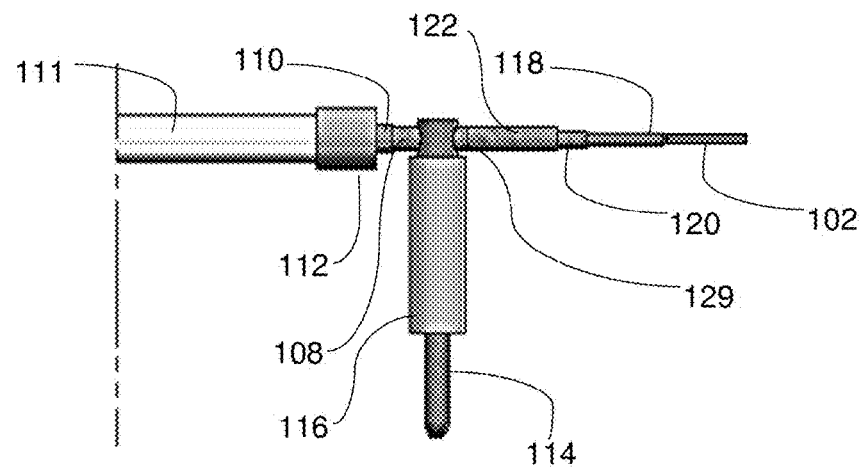
FIGS. 9A, 9B, and 9C, illustrate the assembly of another elongated coupling member with a collar.

As illustrated in FIGS. 1B, and 9A-9C, at least a portion of macro electrode sub-assembly 130 extends distally beyond stopper 112 of shielding tube 111. As illustrated in FIG. 9A, isolating macro sleeve 110 extends distally (away from the tip at proximal end 101), beyond stopper 112, further revealing rigidity-imparting macro cannula 108, extending further. As illustrated in FIGS. 1A, 5, 6A, 6B, and 9A, the portion of macro electrode sub-assembly 130 extending distally beyond stopper 112 of shielding tube 111 is rotatably coupled (see e.g., FIG. 6A) to first (or macro) elongated coupling member 114, first (or macro) elongated coupling member 114 extending transverse to longitudinal axis ($X_L$) of reduced Larsen Effect electrode assembly 100 (see e.g., FIG. 1A) wherein first (or macro) coupling member 114 is configured to be in communication with a first power source, a first transceiver or a first device comprising one or more of the foregoing. In an embodiment, at least one of first (macro) or second (micro) elongated coupling member(s) can be substituted by electrical wires, any other suitable connectors or can alternatively be obviated entirely. As illustrated in FIGS. 6A, 6B, first elongated coupling member 114 is further coupled to first insulating band 116 configured to cover a portion of first elongated coupling member 114.

Figure 9B:
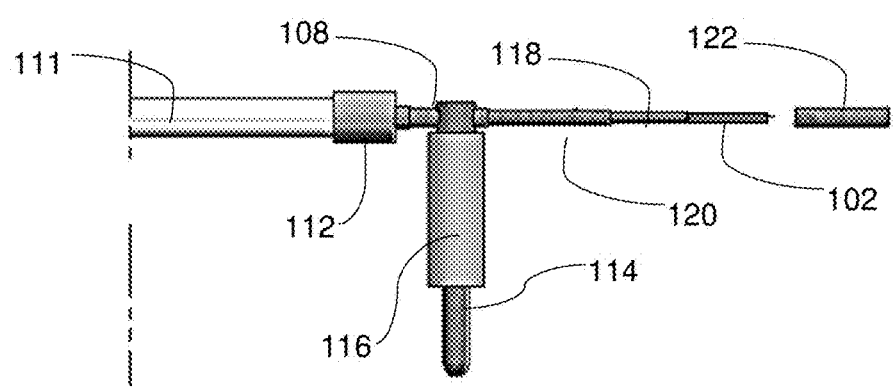
Figure 9C:
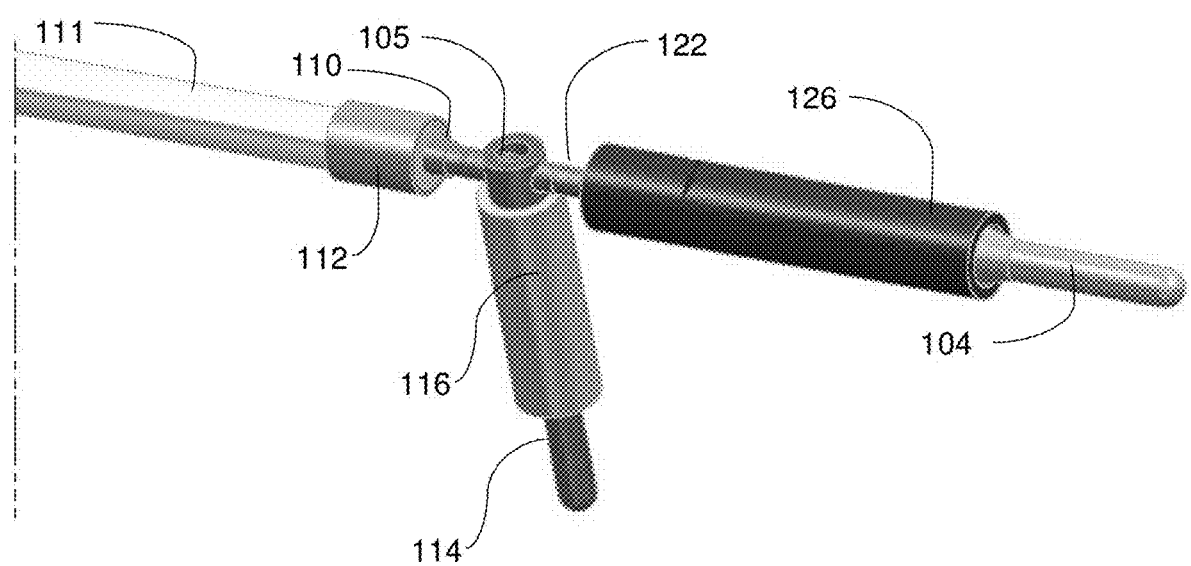

Returning now to FIGS. 1B, 2A, 2B, 7A-7C, and 9A-9C, at least a portion of micro electrode sub-assembly 142 extends distally beyond the distal end 129 of macro electrode sub-assembly 130. As illustrated in FIGS. 1B and 9A-9C, rigidity-imparting micro cannula 120 extends distally (away from tip proximal end 101) beyond distal end 129 of macro electrode sub-assembly 130, revealing isolation macro sleeve 118. As illustrated in FIG. 9B, the exposed isolating macro sleeve 118 at distal end 143 is further coupled to micro collar 122. As illustrated in FIGS. 7A-7C, electrode wire 102 extends proximally, beyond isolating micro sleeve 118 between about 3.5 mm and about 4.5 mm, and beyond rigidity-imparting micro tube 120, 2.5 and about 3.5 mm.

As illustrated in FIGS. 1B, and 9A-9C, the portion of micro electrode sub-assembly 142 extending distally beyond distal end 129 of macro electrode sub-assembly 130 is operably coupled to second (micro) elongated coupling member 104, second (micro) elongated coupling member 104 extending coaxially with longitudinal axis ($X_L$) of reduced Larsen Effect electrode assembly 100 wherein second (or micro) coupling member configured to be in communication with a second power source, a second transceiver or a second device comprising one or more of the foregoing. As illustrated in FIG. 9A, micro collar 122 is operably coupled in an embodiment to rigidity imparting micro cannula 120, operating as a distal limitation on the forward or proximal selectably slidable movement of micro electrode sub-assembly 142. As further illustrated in FIG. 9B, distal end 143 (see e.g., FIG. 7C) of micro electrode sub-assembly 142 exposes insulation-coated wire electrode 102, which can be operably coupled to second (micro) elongated coupling member 104 (see e.g., FIG. 1B). As further illustrated in FIG. 9C, second insulation band 126 can partially cover micro collar 122. It is noted that first and second insulation bands 116, 126 are optional and may not be necessary in all circumstances or embodiments.

Figure 10B:
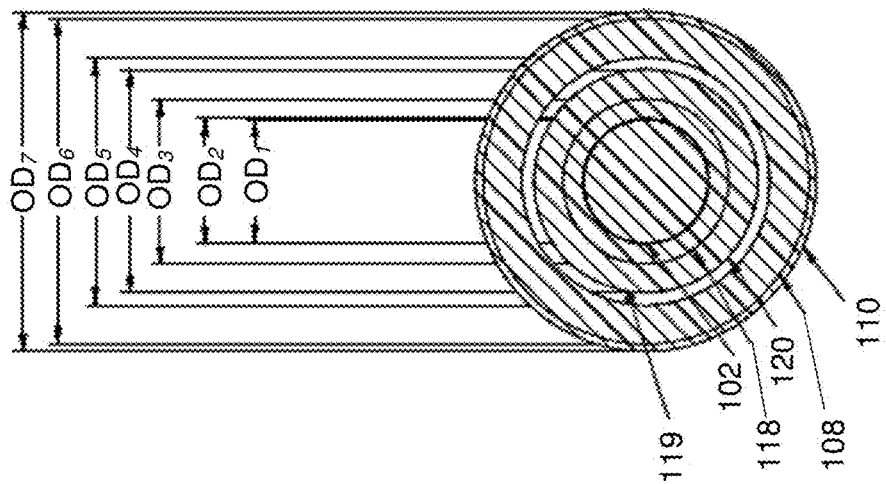
FIGS. 10A and 10B illustrate a Y-Z cross section B of FIG. 1A (FIG. 10B) compared with typical electrode (FIG. 10A)
Figure 10A:
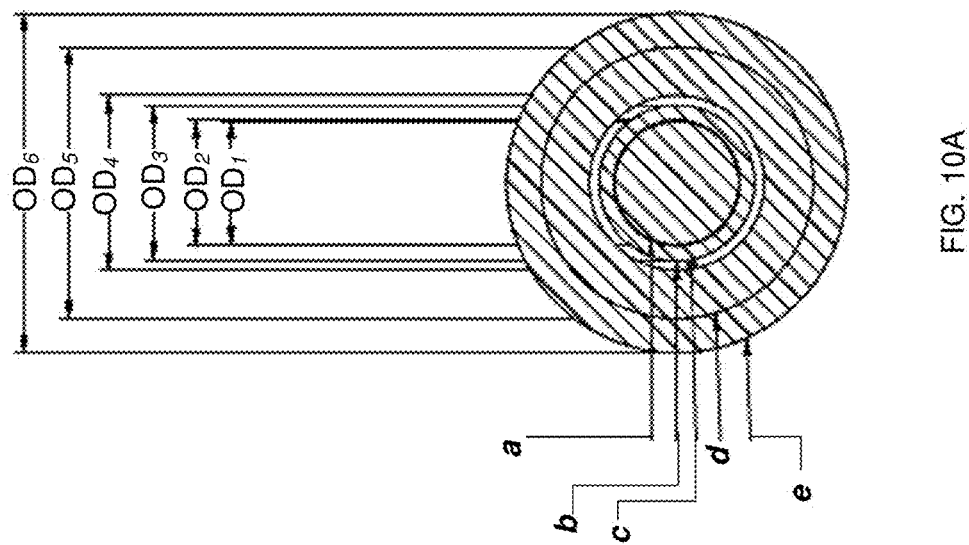

Turning now to FIGS. 10A-10B, illustrating Y-Z cross section B of FIG. 1A. As illustrated in FIG. 1A, of a typical electrode, wherein:

a is an insulation coated ($OD_2$ of 0.26 mm) microelectrode metal ($OD_1$ of 0.254 mm);
b is micro isolation tube ($OD_3$ of 0.32 mm);
c is space ($OD_4$ of 0.36 mm);
d is macro metal tube ($OD_5$ of 0.56 mm); and
e is macro isolation tube ($OD_6$ of 0.7 mm).

Compared with FIG. 10B, illustrating the disclosed reduced Larsen Effect electrode assembly 100, wherein insulation coated ($OD_2$ of 0.26 mm) microelectrode wire ($OD_1$ of 0.254 mm), has isolating micro sleeve 118 ($OD_3$ of 0.34 mm), coaxially disposed rigidity-imparting micro (isolation) cannula 120 ($OD_4$ of 0.46 mm), with annular space 119 ($OD_5$ of 0.51 mm), forming micro electrode sub-assembly 142, disposed within rigidity-imparting macro (isolation) cannula 108 ($OD_6$ of 0.67 mm), having isolating macro sleeve 110 ($OD_7$ of 0.7 mm).

Figure 11:
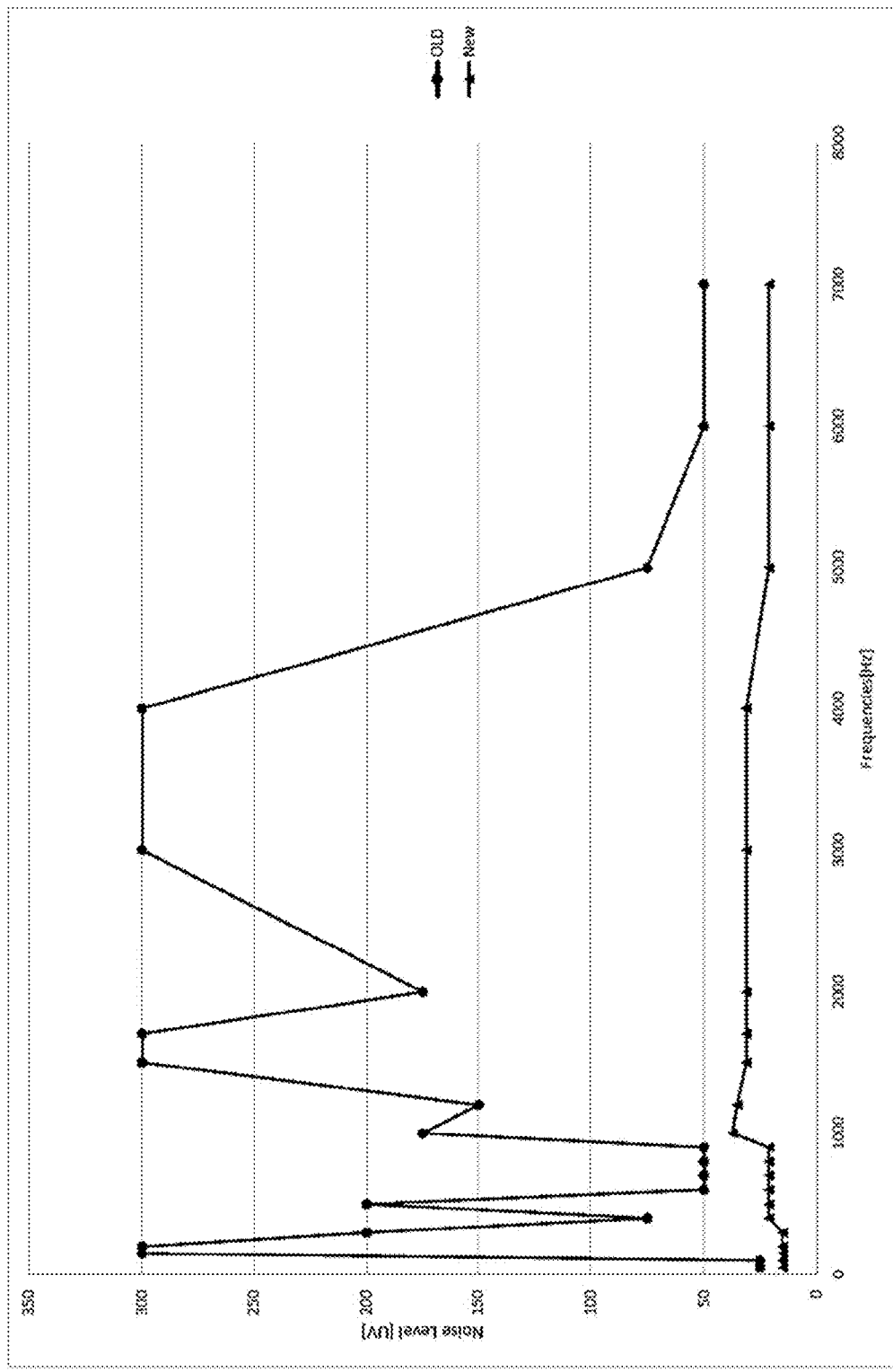
FIG. 11, graph representing the noise levels sensed by the depth electrode of FIG. 1A vs. the depth electrode illustrated in FIG. 10A.

As illustrated, the disclosed electrode has an additional rigid isolation tube without increasing the overall diameter of the electrode. The results in terms of reduction in Larsen effect can be clearly seen in FIG. 11. which is a simplified graph representing the noise levels sensed by the depth electrode 100 of FIG. 1A vs typical prior art depth electrode As illustrated in FIG. 11, a speaker was placed in front of the reference electrode illustrated in FIG. 10A and in front of reduced Larsen Effect electrode assembly 100 constructed and operative in accordance with an embodiment of the present disclosure. Thereafter, the amplitude (sound wave pressure, Db) was changed with the frequency scan. Maximum amplitude where at 800 Hz with amplitude of 90 Db; and a minimum of 30 Db at the amplitude of 9997 Hz. As illustrated, the amplitude is raised from 50 Hz to 800 Hz and then reduced till the 9999 Hz. The resulting noise value was measured and recorded by the electrodes. The resulting graph illustrated in FIG. 11, represents the difference between noise level sensed and recorded by reduced Larsen Effect electrode assembly 100 compared to the electrode illustrated in FIG. 10A, as function of frequency and sound wave pressure. As illustrated, reduced Larsen Effect electrode assembly 100 produces noise level of no more than ±25 µV over frequency range between 50 Hz and 7.0 kHz and no more than ±10 µV over frequency range between 1.0 kHz and 4.0 kHz.

It can also be seen from the graph illustrated in FIG. 11, that in the electrode illustrated in FIG. 10A the noise values as function of frequency reached values of more than 250 µV, whereas in reduced Larsen Effect electrode assembly 100 constructed and operative in accordance with an embodiment of the present disclosure, the amplitude of the noise values as function of frequency only reached values of less than 25 µV, thus providing for approximately ten times noise feedback dampening using reduced Larsen Effect electrode assembly 100 disclosed herein.

Detailed embodiments of the present technology are disclosed herein; however, it is to be understood that the disclosed embodiments are merely exemplary, which can be embodied in various forms. Therefore, specific structural and functional details disclosed herein are not to be interpreted as limiting but merely as a basis for the claims and as a representative basis for teaching one skilled in the art to variously employ the present technology in virtually any appropriately detailed structure. Further, the terms and phrases used herein are not intended to be limiting but rather to provide an understandable and enabling description.

The terms "first." "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the tube(s) includes one or more tube). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

In addition, for the purposes of the present disclosure, directional or positional terms such as "proximal", "distal", "top", "bottom", "upper," "lower," "side," "front," "frontal," "forward," "rear," "rearward," "back," "trailing," "above," "below," "left", "right," "horizontal," "vertical," "upward," "downward," "outer," "inner," "exterior," "interior," "intermediate," etc., are merely used for convenience in describing the various embodiments of the present disclosure.

One or more components may be referred to herein as "configured to," "configured by," "configurable to," "operable/operative to," "adapted/adaptable," "able to," "conformable/conformed to," etc. The terms (e.g. "configured to") can generally encompass active-state components and/or inactive-state components and/or standby-state components, unless context requires otherwise.

Accordingly, provided herein is a reduced Larsen Effect electrode assembly for stimulation and/or recording of electrical signals in a tissue or organ of a subject, the reduced Larsen effect Electrode having a longitudinal axis, a distal end and a proximal end comprising: a shielding tube having an open proximal end and an open distal end, with an open stopper operably coupled to the distal end of the shielding tube; a macro electrode sub-assembly coaxially coupled within the shielding tube, comprising: a rigidity-imparting macro cannula; and an isolating (and/or vibration dampening) sleeve coaxially coupled thereon; and a micro electrode sub-assembly coaxially, slidably coupled within the macro electrode assembly, comprising an insulation-coated electrode wire coaxially coupled along a portion thereof; to an isolating micro sleeve, coaxially coupled within a rigidity-imparting micro cannula, wherein (i) at least a portion of the macro electrode sub-assembly extends distally beyond the stopper of the shielding tube, (ii) the portion of the macro electrode sub-assembly extending distally beyond the stopper of the shielding tube is rotatably coupled to a first elongated coupling member, the first elongated coupling member extending transverse to the longitudinal axis of the reduced Larsen Effect electrode assembly, wherein the first coupling member is operably coupled to the macro electrode sub-assembly and is configured to be in communication with a first power source, a first transceiver or a first device comprising one or more of the foregoing, (iii) the first elongated coupling member is further coupled to a first insulating band configured to cover a portion of the first elongated coupling member, wherein (iv) at least a portion of the micro electrode sub-assembly extends distally beyond the distal end of the macro electrode assembly, (v) the portion of the micro electrode sub-assembly extending distally beyond the distal end of the macro electrode sub-assembly is operably coupled to a second elongated coupling member, the second elongated coupling member extending coaxially with the longitudinal axis of the reduced Larsen Effect electrode assembly wherein the second coupling member is operably coupled to the micro electrode sub-assembly and is configured to be in communication with a second power source, a second transceiver or a second device comprising one or more of the foregoing, (vi) the distal end of the portion of the micro electrode sub-assembly extending distally beyond the distal end of the macro electrode sub-assembly is operably coupled to a micro collar, wherein (vii) rigidity-imparting micro cannula; and the rigidity-imparting macro cannula are separated by an annular space, (viii) the annular space is about 0.01 mm, wherein (ix) the micro electrode sub-assembly coaxially, slidably coupled within the macro electrode assembly is configured to present a variable measuring area at the proximal end of the reduced Larsen Effect electrode assembly, wherein (x) the insulation-coated electrode wire is a tungsten wire, or (xi) of platinum iridium, pure iridium, or stainless steel, (xii) the shielding tube and/or rigidity-imparting macro cannula, and/or rigidity-imparting micro cannula are made of stainless steel, (xiii) the isolation macro sleeve and/or isolating micro sleeve are made of a thermoplastic polymer, (xiv) the polymer is polyimide, polyurethane, poly(divinylfluroride), a polycarbonate, an acrylonitrile/butadiene/styrene copolymer, a poly ether ether ketone, an epoxy, a nylon, or a copolymer and/or derivative thereof comprising one or more of the foregoing, wherein (xv) the rigidity-imparting macro cannula and/or isolating macro sleeve, each have a wall thickness between about 0.01 mm and about 1 mm, (xvi) the rigidity-imparting macro cannula abuts the isolating macro sleeve along the entire length of the isolating macro sleeve, wherein (xvii) the rigidity-imparting micro cannula and/or isolating micro sleeve, each have a wall thickness between about 0.01 mm and about 1 mm, (xviii) the rigidity-imparting micro cannula abuts the isolating micro sleeve along the entire length of rigidity-imparting micro cannula, wherein (xix) the reduced Larsen Effect electrode assembly produces noise level of no more than ±25 µV over frequency range between 50 Hz and 7.0 kHz, or, more specifically, noise level of no more than ±10 µV over frequency range between 1.0 kHz and 4.0 kHz.

While in the foregoing specification the guidance systems for guiding a brain probe to a region of interest and their methods of facilitating have been described in relation to certain preferred embodiments, and many details are set forth for purpose of illustration, it will be apparent to those skilled in the art that the disclosure can be susceptible to additional embodiments and that certain of the details described in this specification and as are more fully delineated in the following claims can be varied considerably without departing from the basic principles of this invention.

What is claimed is:

1. A reduced Larsen Effect electrode assembly for stimulation and/or recording of electrical signals in a tissue or organ of a subject, the reduced Larsen Effect electrode assembly having a longitudinal axis, a distal end and a proximal end comprising:
   a. a macro electrode sub-assembly,
   comprising: a rigidity-imparting macro cannula; and an isolating macro sleeve coaxially coupled thereon; and
   b. a microelectrode sub-assembly coaxially, selectably slidably coupled within the macro electrode sub-assembly, comprising an insulation-coated electrode wire coaxially coupled along a portion thereof to a tube surrounding said insulation-coated electrode wire, wherein said tube is mechanically coupled to said insulation-coated electrode wire to reduce vibrations of said electrode wire resulting from acoustic pressure on the insulation-coated electrode wire, wherein a portion of said insulation: coated electrode wire extends away from said tube for stimulating and/or recording said electrical signals.

2. The electrode assembly of claim 1, wherein at least a portion of the macro electrode sub-assembly is coupled to a first elongated coupling member, the first elongated coupling member extending transverse to the longitudinal axis of the reduced Larsen Effect electrode assembly, wherein the first elongated coupling member is operably coupled to the macro electrode sub-assembly and is configured to be in communication with a first power source, a first transceiver or a first device comprising one or more of the first power source and the first transceiver.

3. The electrode assembly of claim 2, wherein the first elongated coupling member is further coupled to a first insulating band configured to cover a portion of the first elongated coupling member.

4. The electrode assembly of claim 3, wherein at least a portion of the microelectrode sub-assembly extends distally beyond a distal end of the macro electrode sub-assembly.

5. The electrode assembly of claim 4, wherein the portion of the microelectrode sub-assembly extending distally beyond the distal end of the macro electrode sub-assembly is operably coupled to a second elongated coupling member, the second elongated coupling member extending coaxially with the longitudinal axis of the electrode assembly wherein the second elongated coupling member is configured to be in communication with a second power source, a second transceiver or a second device comprising one or more of the second power source and the second transceiver.

6. The electrode assembly of claim 5, wherein a stopper is operably coupled to a distal end of the portion of the microelectrode sub-assembly extending distally beyond the distal end of the macro electrode sub-assembly.

7. The electrode assembly of claim 1, wherein a stopper operably coupled to said microelectrode sub-assembly, configured to limit said selectably slidably movement of said microelectrode sub-assembly within the macro electrode sub-assembly comprises a micro collar.

8. The electrode assembly of claim 1, wherein the microelectrode sub-assembly coaxially, slidably coupled within the macro electrode sub-assembly is configured to present a variable measuring area at the proximal end of the electrode assembly.

9. The electrode assembly of claim 1 wherein the isolating macro-sleeve is a vibration dampening sleeve configured to reduce vibrations of said rigidity-imparting macro cannula.

10. The electrode assembly of claim 1, wherein said insulation-coated electrode wire is made of tungsten, platinum iridium, pure iridium, or stainless steel.

11. The electrode assembly of claim 1, wherein said tube comprises an isolating micro sleeve surrounding said insulation-coated electrode wire.

12. The electrode assembly of claim 11, wherein said tube further comprises a rigidity: imparting micro cannula, wherein said isolating micro sleeve is coaxially-coupled within said rigidity-imparting micro cannula, and wherein said rigidity: imparting micro cannula is fixed to said insulation-coated electrode wire to decrease a flexibility of said insulation-coated electrode wire and prevent building of a resonant wave in response to exposure to vibration resulting from acoustic pressure on the insulation-coated electrode wire.

13. The electrode assembly of claim 12 wherein the rigidity-imparting macro cannula, and/or the rigidity-imparting micro cannula, are made of stainless steel.

14. The electrode assembly of claim 11 wherein the isolation macro sleeve and/or isolating micro sleeve are made of polyimide.

15. The electrode assembly of claim 12, wherein said rigidity imparting micro cannula is formed as a layer on said insulation-coated electrode wire.

16. The electrode assembly of claim 12 wherein the rigidity-imparting micro cannula abuts the isolating micro sleeve along an entire length of the rigidity-imparting micro cannula.

17. The electrode assembly of claim 12, wherein the rigidity-imparting micro cannula and the rigidity-imparting macro cannula are separated by an annular space.

18. The electrode assembly of claim 17, wherein the annular space is between about 0.01 mm and about 0.2 mm.

19. A method for dampening vibrations on an electrode wire during recording of electrical signals from a tissue or organ of a subject, comprising:
 introducing an electrode into a tissue, wherein said electrode comprises (1) a macro electrode sub-assembly comprising a rigidity-imparting macro cannula and an isolating macro sleeve coaxially coupled thereon, and (2) a microelectrode sub-assembly, selectably slidably coupled within the macro electrode sub-assembly, wherein said micro electrode sub-assembly comprising an insulation-coated electrode wire and one or more microelectrode vibration dampening layers, wherein said insulation-coated electrode wire is coaxially coupled along a portion thereof to said one or more microelectrode vibration dampening layers;
 recording electrical signals by said insulation-coated electrode wire; dampening vibrations on said insulation-coated electrode wire during said recording, by said one or more microelectrode vibration dampening layers.

20. A method according to claim 1, wherein said electrode comprises a macro-electrode, wherein said recording comprises recording electrical signals by one or both of said insulation-coated electrode wire and said macro-electrode.

* * * * *